US006942679B1

(12) United States Patent
Terai

(10) Patent No.: US 6,942,679 B1
(45) Date of Patent: Sep. 13, 2005

(54) ANEURYSM TREATING INSTRUMENT

(76) Inventor: Hiromu Terai, 32-1-303, Kawarakitaguchi, Kyotanabe-shi, Kyoto 610-0361 (JP)

( * ) Notice: Subject to any disclaimer, the term of this patent is extended or adjusted under 35 U.S.C. 154(b) by 310 days.

(21) Appl. No.: 10/069,027

(22) PCT Filed: Aug. 24, 2000

(86) PCT No.: PCT/JP00/05670

§ 371 (c)(1),
(2), (4) Date: Feb. 19, 2002

(87) PCT Pub. No.: WO01/15766

PCT Pub. Date: Mar. 8, 2001

(30) Foreign Application Priority Data

Aug. 30, 1999 (JP) ................................ 11-242478

(51) Int. Cl.[7] ............................................ A61M 29/00
(52) U.S. Cl. .................. 606/192; 606/194; 604/103.07
(58) Field of Search ................................ 606/192, 191, 606/194, 195, 198, 108; 604/96.01; 623/1.1–1.2

(56) References Cited

U.S. PATENT DOCUMENTS 4,881,939 A * 11/1989 Newman ..................... 600/31
5,181,911 A * 1/1993 Shturman .............. 604/103.07
6,423,083 B2 * 7/2002 Reiley et al. ............... 606/192

FOREIGN PATENT DOCUMENTS

EP 0 835 673 A2 4/1998
JP 63-84565 A 4/1988
JP 04-129570 A 4/1992
WO WO 94/26206 A1 11/1994

OTHER PUBLICATIONS

English translation of International Preliminary Examination Report dated Nov. 13, 2001 in International Application No. PCT/JP00/05670 filed Aug. 24, 2000.

* cited by examiner

*Primary Examiner*—Vy Bui
(74) *Attorney, Agent, or Firm*—Frishauf, Holtz, Goodman & Chick, P.C.

(57) ABSTRACT

The object of the present invention is to provide an improved balloon catheter for curing aneurysms, and particularly dissecting aortic aneurysms, promptly and without surgical treatment, the therapeutic appliance for treating dissecting aortic aneurysms comprising providing a stretchable bag-like element on and along the end portion of a catheter, the bag-like element being in the form of a flat film when not holding a fluid inside and in the form of a tube when holding a fluid inside, and the inside film and outside film that compose the bag-like element are partially joined.

7 Claims, 6 Drawing Sheets

3 3 3 11 1 11 2 3b 21 3a 21 1 21 3

ANEURYSM TREATING INSTRUMENT

This application is a U.S. National Phase Application under 35 USC 371 of International Application PCT/JP00/05670 (not published in English) filed Aug. 24, 2000.

TECHNICAL FIELD

The present invention relates to a therapeutic appliance suitable for treatment of aneurysms, and particularly, dissecting aortic aneurysms.

BACKGROUND ART

Although aneurysms, and particularly dissecting aortic aneurysms, refer to a state in which an ulceration has occurred in the tunica intima of the aorta, said tunica intima is partially ruptured, blood flows from that site inside the wall of the aorta and said aorta wall is dissected into two layers (the blood pathway that has formed between the blood vessel wall and said separated tunica intima is referred to as a “pseudo cavity”, while the space inside the tunica intima which is the inherent blood pathway is referred to as the “true cavity”), if this condition is left untreated, the outer wall of the aorta eventually ruptures leading to death.

The method for treating dissecting aortic aneurysms has conventionally only consisted of suturing and closing the ruptured portion of the above tunica intima (referred to as the “entry”, while the blood outlet of the “pseudo cavity” is referred to as the “reentry”) by surgery as an emergency procedure, or by excising the dissected blood vessel and replacing said excised portion with an artificial blood vessel.

However, in the above suturing and closing procedure, due to the fragile nature of the tissue around the entry, the suturing and closing procedure itself is extremely difficult. Moreover, even if suturing and closing procedure are successful and further risk is able to be avoided at least for the time being, there are many cases in which the patient dies within five years after surgery. On the other hand, in the case of replacing the dissected blood-vessel with an artificial blood vessel, the patient is subjected to considerable burden to the extensive nature of the procedure, and in the case the “pseudo cavity” is long, replacement with an artificial blood vessel cannot be applied since it ends up obstructing the furcation of blood vessels that branch from the aorta.

Recently, an appliance and method using that appliance have been reported as a non-surgical method in which a flexible, stretchable bag is attached to the end of a flexible catheter and expanded with a fluid injected from the base end of the catheter to form a hollow, cylindrical balloon. The balloon catheter, composed by laminating a plurality of hollow, tubular bodies, which are stretched by said stretchable bag due to said fluid, in the direction of the central axis around said stretchable bag, is inserted into the dissected portion of the tunica intima, and the tensile strength of said stretchable bag is then used to reduce said pseudo cavity, thereby allowing blood to flow to the true cavity (Japanese Patent No. 2546829). Although the method using this appliance is superior to methods of the prior art with respect to allowing closure of the entry in the acute phase while maintaining blood flow toward periphery, the fabrication of said hollow tubular body and its attachment to said stretchable bag are intricate and bothersome. Moreover, there is still room for further examination with respect to clinical application since, among other factors, there are limits on the degree to which the volume it occupies can be minimized when inserting into a blood vessel.

DISCLOSURE OF INVENTION

The object of the present invention is to provide an improved balloon catheter for curing aneurysms, and particularly dissecting aortic aneurysms, promptly and without surgical treatment.

Namely, the therapeutic appliance of the present invention is characterized by being a dissecting aortic aneurysm therapeutic appliance comprising the providing of a stretchable bag-like element on and along the end portion of a catheter, said bag-like element being in the form of a flat film when not holding a fluid inside and in the form of a tube when holding a fluid inside, and the inside film and outside film that compose said bag-like element are partially joined.

Here, the reason for partially joining the inside film and outside film that compose the above bag-like element is to prevent constriction and occlusion of the blood flow path (which is the hollow portion of the tubular body formed by said expanded bag-like element) caused by over-expansion of the central portion of said bag-like element as compared with the edges. In addition, said bag-like element being in the form of a flat film refers to the state in which the inside film and outside film that compose said bag-like element are capable of surface contact, while said bag-like element being in the form of a tube refers to the state in which said inside film and said outside film are separated with the exception of their joined portions, and said bag-like element is substantially in the form of a tube.

A catheter wrapped with the bag-like element in the form of a flat film (which may be easily understood by likening said bag-like element in the form of a flat film to a flag, and likening said catheter to a pole to which the flag is attached) having the above structure (and its length, namely the dimension of the catheter in the axial direction, should be equal to or greater than the length in the direction of the long axis of the blood vessel of the entry that is to be closed) is inserted percutaneously from the femoral artery, and then a fluid such as physiological saline is filled through the catheter into said bag-like element, namely into the space between the inside film and outside film that compose said bag-like element when the bag-like element has reached the entry of the dissected cavity. When said bag-like element in the form of a flat film is then expanded, said dissected tunica intima is pressed against the blood vessel wall by said outside film of said expanded bag-like element, thereby closing said entry. On the other hand, since the inside film of said expanded bag-like element composes the inside cavity wall (the space between said outside film and said inside film is made to imitate the wall of a tube), said bag-like element substantially becomes a tubular body, and its hollow portion serves to ensure blood flow toward periphery by serving as a blood flow path. Here, the width of said bag-like element, namely the outer diameter of the bag-like element when in the form of said tube, should be set to be slightly larger than the inner diameter of the blood vessel of the site where the therapeutic appliance of the present invention is to be applied. As a result of maintaining a state in which entry is closed while ensuring blood flow toward periphery in this manner, thrombogenesis of the pseudo cavity progresses and once said pseudo cavity has been adequately obstructed with thrombi, said bag-like element is flattened by discharging fluid from inside said bag-like element, and then either again wrapped around the catheter or extracted from the affected area while still flattened, thereby allowing the disease to be treated without resulting in an artificial object remaining in the body.

BEST MODE FOR CARRYING OUT THE INVENTION

The following provides a detailed explanation of the present invention with reference to the drawings showing several examples of embodiments of the present invention.

Figure 1:
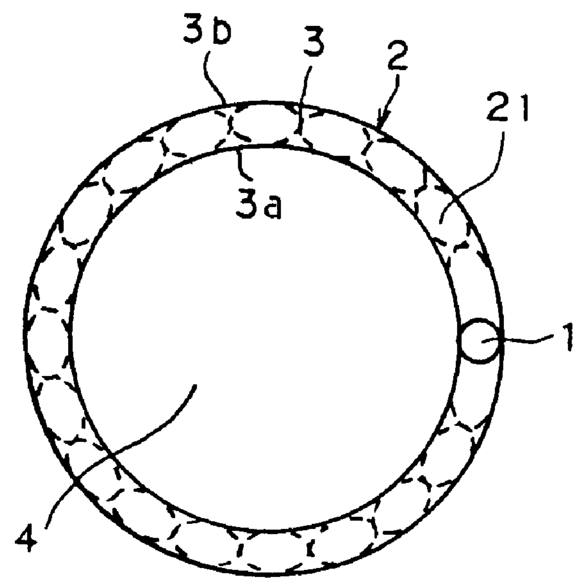
FIG. 1 is a plan view showing an example of one mode of the thrapeutic appliance of the present invention (when fluid is filled).
Figure 2:
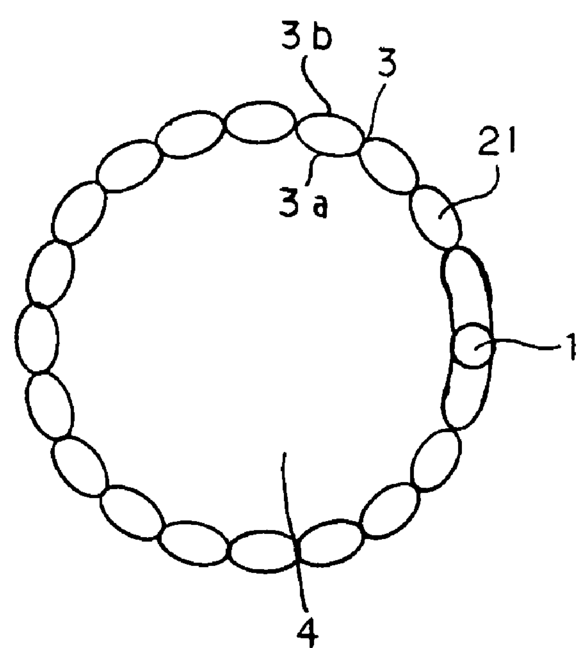
FIG. 2 is a cross-sectional view showing an example of one mode of the thrapeutic appliance of the present invention (when fluid is filled).
Figure 3:
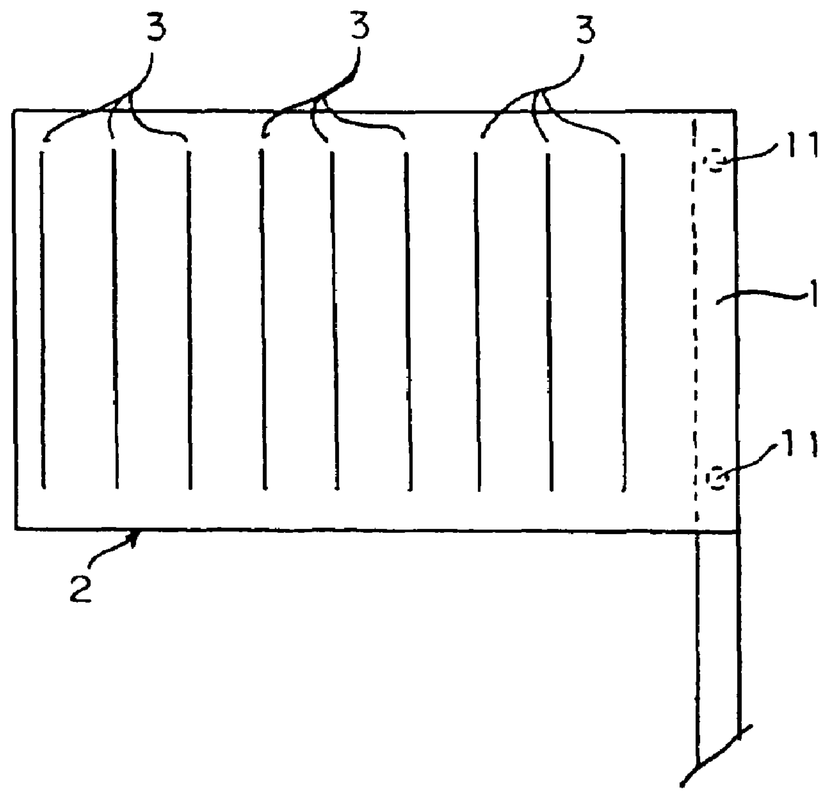
FIG. 3 is a side view showing an example of one mode of the therapeutic appliance of the present invention (when fluid is not filled).

FIGS. 1 to 3 show an embodiment of the therapeutic appliance of the present invention. Here, FIGS. 1 and 2 show the state in which a fluid is filled inside the bag-like element causing said bag-like element to expand (FIG. 1: plan view, FIG. 2: cross-sectional view—sectioned in the plane that intersects the axis of catheter 1 and contains the joined portion to be described later), while FIG. 3 shows the state in which a fluid is not filled inside said bag-like element or the state after said fluid has been discharged (the state in which said bag-like element is pulled at the point where its length, namely circumferential length, becomes half in the direction of width of said bag-like element, namely the direction that is perpendicular to the axis of catheter 1, and the inner film that composes said bag-like element makes surface contact). Being in the form of a tube refers to that which describes the state of said bag-like element shown in FIGS. 1 and 2 (reference numeral 4 indicates the hollow portion). Furthermore, each drawing is depicted with the size of each member exaggerated so as to facilitate a clear understanding of the overall composition. Thus, the dimensional ratios between each member are not the actual dimensional ratios (and this is to apply similarly hereinafter). In addition, indication of the thickness of each member or site is omitted for the purpose of avoiding excessively complexity of the drawing (and to apply similarly hereinafter unless otherwise).

In the drawings, reference numeral 1 indicates a flexible, tubular catheter made of rubber or plastic (specific examples of materials of which include polyethylene, polypropylene, polyurethane, polyvinyl chloride, polyvinyl alcohol, polyamide, silicone, synthetic rubber and fluororesin, and to apply similarly hereinafter). On the end of this catheter (although this end portion is normally "blind" for the purpose of preventing outflow of fluid, in the case of introducing a manipulating appliance into said catheter, a plate member may be provided in which a hole is formed that enables the prevention of the outflow of fluid while also enabling said manipulating appliance to be inserted and removed; in addition, although said end portion and the edges of the bag-like element are depicted as being in the same plane in the drawings, said end portion may also be of a shape that slightly protrudes from said edges in consideration of greater ease of fabrication and so forth, and this is to apply similarly hereinafter), bag-like element 2 is provided that is composed of a material having flexibility (specific examples of materials include the same materials as those of the above-mentioned catheter, and this is to apply similarly hereinafter). (As shown in FIGS. 1 to 3, the mode of this bag-like element 2 is such that said catheter is wrapped within both edges of inside film 3*a* and outside film 3*b* that compose said bag-like element. Naturally, both edges of said films may also be adhered and fixed to the peripheral surface of said catheter so as to prevent leakage of fluid. In addition, although the thickness of said bag-like element when a fluid is filled, namely the distance between inside film 3*a* and outside film 3*b*, is depicted in the drawings to be equal to the outer diameter of said catheter, said bag-like element is not limited to this mode, and for example, may be in the modes shown in FIGS. 4 and 5. Moreover, the inside film of said bag-like element may be provided on and along the peripheral surface of the catheter. Furthermore, in the case of employing the mode shown in FIG. 4, when attaching said bag-like element to said catheter, said catheter should be arranged so that it also passes through the upper edge of said bag-like element, and said bag-like element should be adhered and fixed to said catheter with heat or adhesive, etc. at the site at which said catheter passes through said bag-like element. In addition, in the case of employing the mode shown in FIG. 5, in addition to the attachment method like that of the mode shown in FIG. 4, a method can also be employed in which said bag-like element is adhered and fixed to said catheter with heat or adhesive, etc. at the site where there is contact between said outside film and the peripheral surface of said catheter.) When percutaneously guiding this therapeutic appliance to the affected site, this is performed in the state in which said bag-like element in the form of a flat film is wrapped around said catheter. On the other hand, when removing the therapeutic appliance from the affected site, this may be performed after wrapping said bag-like element that has again been flattened around said catheter by manual force such as, for example, rotating said catheter. In addition, since said bag-like element has flexibility, said flattened bag-like element may be removed with said catheter while remaining in that form. Here, the portion represented with a plurality of lines drawn parallel to the axis of said catheter (see FIG. 3) represent joined portions 3 between inside film 3*a* and outside film 3*b* that compose said bag-like element (and are joined linearly in this case;

furthermore, a reference numeral is only depicted at one location in order avoid excessive complexity of the drawings in FIGS. 1 and 2). Since this joining procedure can be carried out easily in the case of using a heat-fusible material such as polyethylene, polypropylene, polyurethane or silicone for the inside and outside films, the use of such materials is advantageous. Furthermore, it is preferable to either mutually join each edge of each film in advance or form each film into a single unit to form a bag-like element. In the drawings, reference numeral 11 indicates filling and discharge ports for fluid to and from the inside of said bag-like element that are formed in the catheter so as to penetrate its wall surface. Although four round holes serving as said fluid filling and discharge ports are shown in the drawings, with two present on the back side, there are no particularly restrictions on their number and shape provided they result in smooth movement of fluid. These ports should be suitably selected from those having various shapes such as notches (as in the modes shown in FIGS. 5 and 6), slots or slits (as in the mode shown in FIG. 7).

Figure 6:
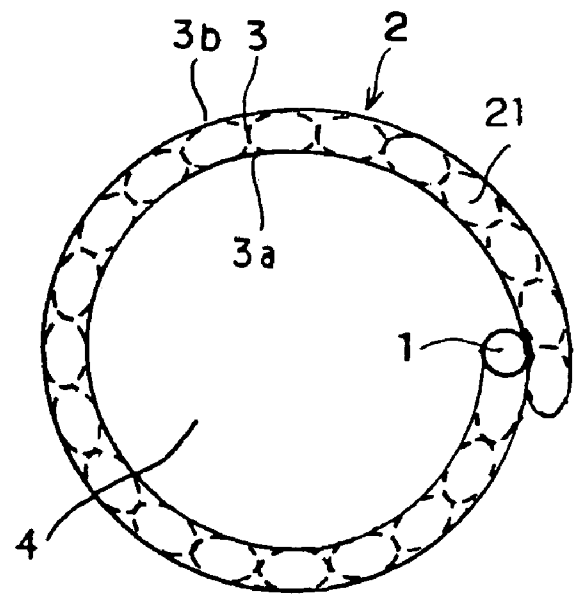
FIG. 6 is a plan view showing an example of another mode of the therapeutic appliance of the present invention (when fluid is introduced inside the body).
Figure 7:
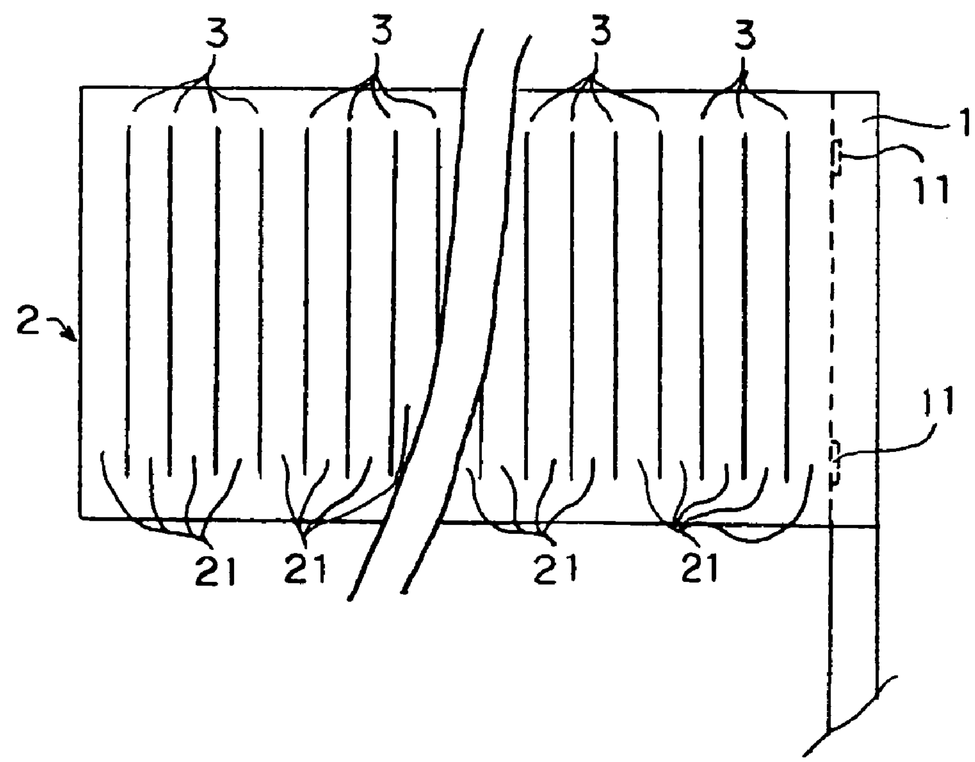
FIG. 7 is a side view showing an example of further mode of the therapeutic appliance of the present invention (when fluid is not filled and when fluid is filled outside the body).

FIGS. 6 and 7 show another embodiment, and particularly an embodiment having a bag-like element of a different form than the previously described embodiment. Here, FIG. 6 shows the state in which fluid is filled into bag-like element 2 causing said bag-like element to expand in the body (plan view, while FIG. 7 shows the state in which fluid is not filled into said bag-like element or after said fluid has been discharged. In this embodiment, when fluid is received inside said bag-like element, said bag-like element takes on the shape of a plate (and more accurately, a curved plate) as shown in FIG. 6 (but in the form of a flat plate when fluid is received outside the body). This is because when said bag-like element is guided to the affected site in the state in which it is wrapped around catheter 1 and fluid is filled into said bag-like element when it has reached the entry of the dissected cavity, since outside film 3*b* of said bag-like element is subjected to the reaction force from the blood vessel inner wall, said bag-like element that is in the form of a plate in the free load state is inevitably deformed to a shape that follows the blood vessel wall. Furthermore, the width of said bag-like element should be set so that one edge of the curved plate-shaped bag-like element (side that is provided on and along the catheter) and the other edge are slightly overlapping. The therapeutic appliance of this mode is, as a general rule, used in the state in which said bag-like element is wrapped around said catheter both when guiding to the affected site and when removing from the affected site. (This is because, since "wrapping" can be performed more tightly as compared with that in the mode shown in FIGS. 1 to 3, the proportion of the cross-sectional area of the flattened therapeutic appliance that occupies the blood vessel cross-section can be reduced, thereby allowing insertion and removal of the therapeutic appliance to and from the affected site to be carried out more smoothly.)

In FIG. 7, although catheter 1 is arranged on the right edge of said bag-like element so that it is contained inside (in this mode, wrapping of said bag-like element onto said catheter, for example wrapping by rotating said catheter, can be carried out smoothly), the position where said catheter is arranged is not limited to the edge, but rather, for example, may be arranged closer to the central portion of said bag-like element, namely near the position of the broken line in FIG. 7. In this case, since it becomes difficult to smoothly wrap said bag-like element onto said catheter, it is preferable to provide a spring material that applies force in the direction of, wrapping on at least the upper and lower edges of said bag-like element (although not shown in the drawings, this material should be suitably selected from materials that do not have a detrimental effect on the body).

Figure 8:
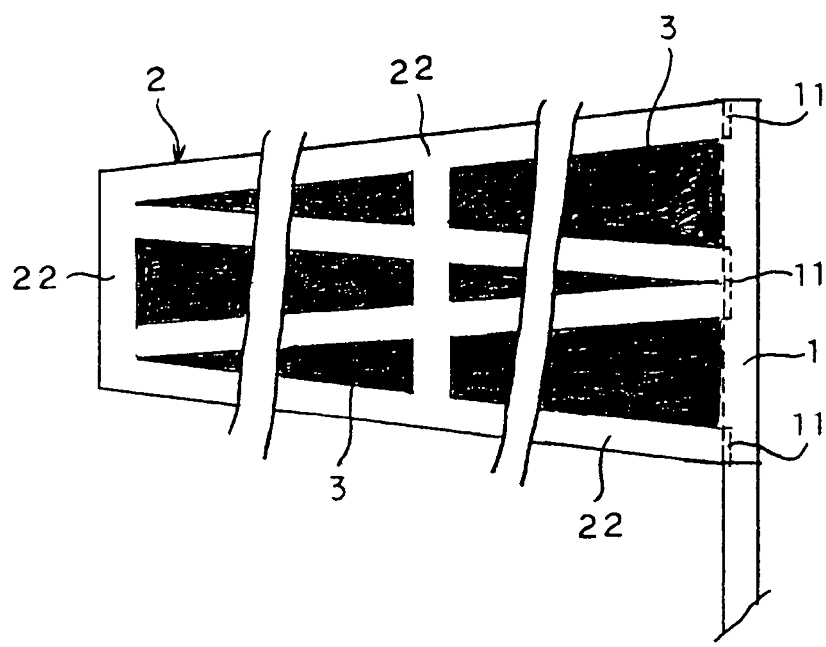
FIG. 8 is a side view showing another example of further mode of the therapeutic appliance of the present invention (when fluid is not filled and when fluid is filled outside the body).
Figure 9:
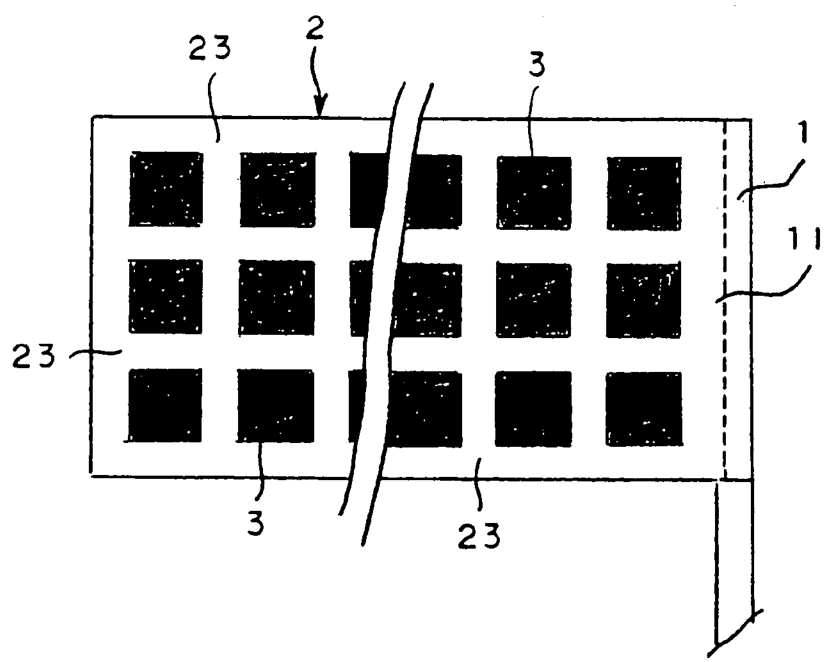
FIG. 9 is a side view showing yet an additional example of further mode of the therapeutic appliance of the present invention (when fluid is not filled and when fluid is filled outside the body).

FIGS. 8 and 9 show still another embodiment, and particularly an embodiment having a different form of joining the inside and outside films that compose the bag-like element. In these drawings, the blacked out portions indicate the joined portions of said inside and outside films (surface joining), while the other portions indicate fluid filling and discharge paths 22 and 23 for expanding said bag-like element. (In the drawings, reference numerals are provided only for those representative portions. Furthermore, the above paths are indicated with reference numeral 21 in the mode shown in FIGS. 1 to 5. Only indicating a reference numeral for a representative portion is the same as in FIGS. 8 and 9.) Naturally, the mode in which said inside and outside films are joined allows smooth filling and discharge of fluid to or from said bag-like element, and is not limited to that shown in these drawings provided considerations are given so that hollow portion 4 of the tubular body formed as a result of filling fluid into said bag-like element when said filling is performed is not constricted or obstructed. In addition, although the mode shown in the drawings is depicted based on applying to the embodiment shown in FIGS. 6 and 7, the state in which the inside and outside films are joined (surface joining) can also be applied to the embodiment shown in FIGS. 1 to 5.

Figure 10:
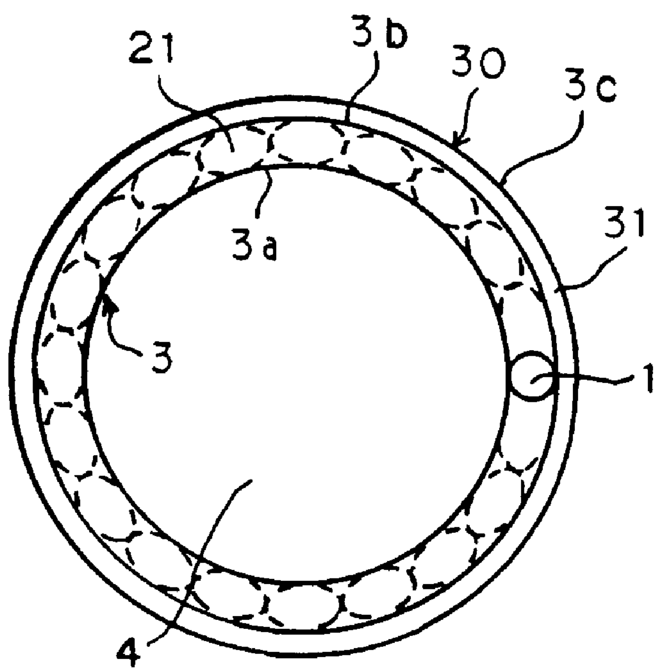
FIG. 10 is a plan view showing an example of still another mode of the therapeutic appliance of the present invention.
Figure 11:
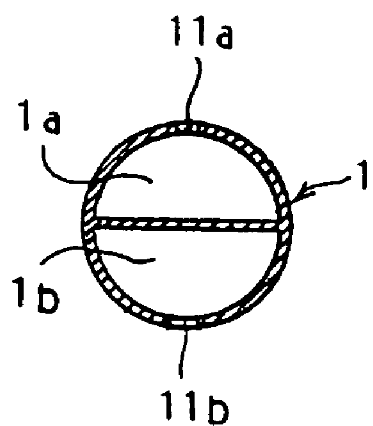
FIG. 11 is a cross-sectional view showing an example of the catheter of the therapeutic appliance of the present invention (sectioned in the plane that passes through the opening and is perpendicular to the axis of said catheter).

FIG. 10 shows still another embodiment, and particularly an embodiment having another different bag-like element. Namely, an embodiment is shown in which an additional film 3*c* (the same material can be used as that of the original bag-like element) is added further to the outside of outside film 3*b* of said bag-like element, and bag-like element 30 is provided further to the outside of said bag-like element. (This means that outside film 3*b* of said bag-like element composes the inside film of this additional bag-like element 30. Furthermore, the left and right edges of said additional film should be joined in advance, and its upper and lower edges should be joined to the upper and lower edges of outside film 3*b* of bag-like element 3. This additional bag-like element is not provided with a joined portion like that of the original bag-like element.) In the drawing, although a bag-like element of the mode shown in FIGS. 1 to 3 is depicted as the original bag-like element 3, it goes without saying that a bag-like element of the mode shown in FIGS. 6 and 7 as well as a bag-like element of the mode shown in FIGS. 8 and 9 can naturally also be used as bag-like element 3 of this mode. However, in the case of using the bag-like element of the mode shown in FIGS. 6 and 7 for the original bag-like element 3, since the expansion of that bag-like element is restricted by additional film 3*c* even if fluid is filled inside when outside the body, it naturally does not take on the form of a flat plate. According to this embodiment, the functions of pressing and closing the entry are further improved with respect to the point of more faithfully tracing the surface shape of the blood vessel inner wall (that which makes contact with the blood vessel inner wall is this additional film 3*c*). Moreover, if a material having a higher degree of flexibility than the material composing the original bag-like element is selected for this additional film 3*c*, this embodiment offers the advantage of eliminating the need to precisely set the outer diameter during expansion of original bag-like element 3. Here, the simplest method by which fluid is filled into both bag-like elements consists of partitioning the lumen of original catheter 1 into two spaces 1*a* and 1*b*, and providing openings 11*a* and 11*b* to each space. (Refer to FIG. 11. Furthermore, the manner in which original bag-like element 3 and catheter 1 are arranged is preferably the mode shown in FIG. 5, namely the state in which the inside of original bag-like element 3 is in contact with the peripheral surface of said catheter. In this case, opening 11*b* is arranged in said catheter so as to present in this contact surface. Furthermore, it goes without saying that it is necessary to provide a hole corresponding to this opening 11*b* in bag-like element 3*b*.) Naturally, dedicated catheters may also be provided for each.

TEST EXAMPLE

Using six mongrel adult dogs having body weights of 17–20 kg (aorta inner diameter: 13–18 mm), dissecting aortic aneurysms were produced in the aorta ascendens of each animal.

Figure 4:
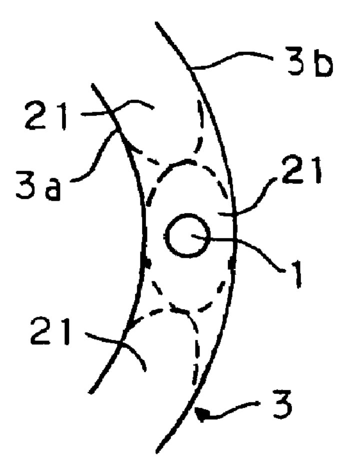
FIG. 4 is a partially enlarged plan view showing an example of the mutual positional relationship between the catheter and bag-like element of the therapeutic appliance of the present invention.
Figure 5:
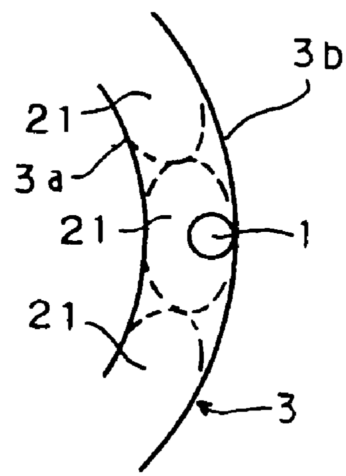
FIG. 5 is a partially enlarged plan view showing another example of the mutual positional relationship between the catheter and bag-like element of the therapeutic appliance of the present invention.

The therapeutic appliance of the present invention was inserted and arranged into the lesion produced in each animal in accordance with the procedure previously described. (The mode of the therapeutic appliance of the present invention was the mode shown in FIGS. 1 to 3. An existing product provided in advance with an opening in one edge was used for bag-like element 2. Furthermore, the specifications of each member consisted of: (1) catheter: polyurethane, outer diameter: 2.0 mm, inner diameter: 1.5 mm, insertable length: 350 mm; (2) bag-like element: polyethylene, film thickness: 0.05 mm, length: 20 mm, outer diameter and inner diameter (when filled with fluid): 15 mm and 9 mm, respectively; (3) interval of joined portions in bag-like element: 5 mm; (4) shape of fluid filling and discharge ports: four round holes having a diameter of 0.5 mmϕ; and, (5) manner of attachment of bag-like element to catheter: the catheter was arranged as shown in FIG. 4, the leading end of said catheter was made to protrude from the upper end of said bag-like element, and the bag-like element was adhered to the catheter with adhesive at the site at which the catheter passed through the bag-like element.)

Closure of the entry was confirmed by observing by angiography on the following day. In addition to closure of the entry, closure of the pseudo cavity was also confirmed to have occurred completely in observation (angiography) of the state of the aneurysm 10 days after the procedure.

INDUSTRIAL APPLICABILITY

As has been described above, according to the therapeutic appliance of the present invention, with respect to the surgical procedure, since only a catheter is inserted into a blood vessel, (1) there is little burden on the patient, and (2) dissecting aortic aneurysms can be treated safely. Consequently, it enables treatment to be performed effectively even on cases such as elderly patients for which surgery is difficult in terms of their stamina, the number of whom is expected to increase in the future. Moreover, since the bag-like element provided on and along the catheter is formed by partially joining the inside and outside films that compose it in the form of linear or surface joining, the therapeutic appliance of the present invention can be manufactured easily, and since it is guided to the affected area through a blood vessel in the state in which said flattened bag-like element is wrapped around said catheter, its handling is also easy.

What is claimed is:

1. A therapeutic appliance for treating dissecting aortic aneurysms, said appliance comprising:

a stretchable bag-like element provided on and along an end portion of a catheter, said stretchable bag-like element having an inside film and an outside film which are directly joined at a plurality of linear joined portions, each of said linear joined portions being substantially parallel to a longitudinal axis of the catheter, and said linear joined portions being spaced apart in a direction perpendicular to the longitudinal axis of the catheter;

wherein said bag-like element is shaped as a flat film when not holding a fluid inside and is shaped as a tube when holding a fluid inside; and wherein the linear joined portions do not extend to a front edge and a rear edge of the bag-like element.

2. The therapeutic appliance according to claim 1, further comprising an additional film on an outside surface of the bag-like element, and wherein said additional film defines a space between the additional film and the outside film for holding fluid therein.

3. A therapeutic appliance for treating dissecting aortic aneurysms, said appliance comprising:

a stretchable bag-like element provided on and along an end portion of a catheter, said stretchable bag-like element being substantially rectangular and comprising an inside film and an outside film which are directly joined at a plurality of linear joined portions, each of said linear joined portions being substantially parallel to a longitudinal axis of the catheter, and said linear joined portions being spaced apart in a direction perpendicular to the longitudinal axis of the catheter;

wherein said bag-like element is shaped as a flattened film when not holding a fluid inside and is shaped as a flat plate when holding fluid in a free load state; and wherein the linear joined portions do not extend to a front edge and a rear edge of the bag-like element.

4. The therapeutic appliance according to claim 3, wherein a spring material is provided perpendicular to an axis of the catheter and applies force to at least a front edge and a rear edge of the bag-like element so as to wrap the bag-like around the catheter in the free load state.

5. The therapeutic appliance according to claim 4, further comprising an additional film on an outside surface of the bag-like element, and wherein said additional film defines a space between the additional film and the outside film for holding fluid therein.

6. The therapeutic appliance according to claim 3, wherein a spring material is provided perpendicular to the axis of the catheter and applies force to at least the front edge and the rear edge of the bag-like element so as to wrap the bag-like element around the catheter when the bag-like element is not filled with fluid.

7. The therapeutic appliance according to claim 3, further comprising an additional film on an outside surface of the bag-like element, and wherein said additional film defines a space between the additional film and the outside film for holding fluid therein.

* * * * *